United States Patent
Von Mandach

(10) Patent No.: US 7,775,793 B2
(45) Date of Patent: Aug. 17, 2010

(54) ORTHODONTIC BRACKET

(76) Inventor: Christoph Von Mandach, Bahnhofstrasse 5, CH-5200 Brugg (CH)

( * ) Notice: Subject to any disclaimer, the term of this patent is extended or adjusted under 35 U.S.C. 154(b) by 316 days.

(21) Appl. No.: 11/568,448

(22) PCT Filed: Feb. 8, 2005

(86) PCT No.: PCT/CH2005/000067

§ 371 (c)(1),
(2), (4) Date: Oct. 10, 2007

(87) PCT Pub. No.: WO2005/104982

PCT Pub. Date: Nov. 10, 2005

(65) Prior Publication Data

US 2008/0038683 A1 Feb. 14, 2008

(30) Foreign Application Priority Data

Apr. 28, 2004 (CH) .................................... 0744/04

(51) Int. Cl.
*A61C 3/00* (2006.01)
*A61C 5/00* (2006.01)
(52) U.S. Cl. ................................ 433/8; 433/11; 433/13
(58) Field of Classification Search ................. 433/8–17
See application file for complete search history.

(56) References Cited

U.S. PATENT DOCUMENTS

| 4,209,906 | A | | 7/1980 | Fujita |
|---|---|---|---|---|
| 5,125,832 | A | | 6/1992 | Kesling |
| 5,474,445 | A | | 12/1995 | Voudouris et al. |
| 5,711,666 | A | | 1/1998 | Hanson et al. |
| 5,885,074 | A | * | 3/1999 | Hanson ........................ 433/13 |
| 6,368,105 | B1 | * | 4/2002 | Voudouris et al. ............. 433/11 |

FOREIGN PATENT DOCUMENTS

EP 1090604 A2 4/2001

\* cited by examiner

*Primary Examiner*—Cris L Rodriguez
*Assistant Examiner*—Eric Rosen
(74) *Attorney, Agent, or Firm*—Janet Sleath; Speckman Law Group PLLC

(57) ABSTRACT

An orthodontic bracket is provided. The bracket includes a rear wall coming to rest on a buccal or lingual tooth surface; and two guide surfaces running at right angles to one another, for guiding an archwire with a rectangular cross section, wherein the two guide surfaces are arranged distanced to the rear wall. A first gingival web runs below the first guide surface and at least one second occlusal web runs above the first guide surface, with a second passage being left free between the first web and the rear wall, and a first passage being left free between the second web and the rear wall.

13 Claims, 11 Drawing Sheets

US 7,775,793 B2

ORTHODONTIC BRACKET

CROSS REFERENCE TO RELATED APPLICATIONS

This application claims priority under 35 U.S.C. §365 (a) to International Patent Application No. PCT/CH2005/000067, filed Feb. 8, 2005, and under 35 U.S.C. §120 to International Patent Application No. PCT/CH2005/000067, filed Feb. 8, 2005, which claims priority to Swiss Patent Application No. 744/04, filed Apr. 28, 2004.

FIELD OF THE INVENTION

The present invention relates to an orthodontic bracket with a rear wall corning to lie on the buccal or lingual tooth surface, and exactly two guide surfaces running at right angles to one another for guiding an archwire with a rectangular cross section.

BACKGROUND OF THE INVENTION

Orthodontic treatment is generally carried out by way of orthodontic brackets, with which the positioning of an individual's teeth are brought into an optimising alignment. In particular, there are three correcting measures or movements, crown angulation in a mesio-distal direction which is known as tipping, angulation or tilting; crown angulation in the bucco-lingual direction which is indicated as torque; and rotation with regard to the occlusal view. The bracket forms the engagement point for all forces to carry out these movements. An archwire serves as a force-exerting or force-transmitting means on the brackets and it must be held or guided on or in the orthodontic bracket. The fixation of the archwire on the orthodontic bracket may be affected in different ways. Thus the brackets may be provided with suitable tubelets, hoes, or wings. These fixation means then permit the archwire to be fixed in a desired position relative to the orthodontic bracket by way of metal ligatures, rubber O-rings, or U-springs. Most orthodontic bracket known in the art is provided with a slot, into which the archwire may be inserted more or less with a positive fit. In order to carry out a correction as accurately as possible, in the slot, a type of groove shaped in a U-shaped manner must fit together with the archwire to achieve a positive fit. However, considering the fact that the different angulations, specifically the tipping or the torque, should achieve angular corrections per tooth of 0°-13° or of −12° to 28° respectively, and simultaneously a rotation is take place, the shaping of the archwire unavoidably results in the influencing of the forces on adjacent teeth, since in most cases the slot leads to an over definition which results in undesired influences.

In general, there are two types of brackets the first type having arch thickness of 0.018 inches (0.46 mm) times 0.022 inches (0.56 mm), and the second type having arch thickness of 0.002 inches (0.56 mm) times 0.025 inches (0.65 mm). There are also a large number of different tubelets for the 8 molars in the lower and upper jaw. U.S. Pat. No. 5,125,832 describes a bracket which permits an orthodontic archwire more play than all previously known edgewise brackets. The bracket permits an orthodontic manner of treatment which combines the great advantages of different bracket types. The fine adjustment at the end of the treatment, in particular the individual inclination or torque control is a problem in all systems since orthodontic archwires with a large cross section are required for this, thus provoking large interdental forces even with small bending.

An ultimate and very complicated solution for achieving the greatest possible precision is described by Dirk Wiechmann. He allows brackets to be manufactured for each individual tooth and each individual patient by way of CAD/CAM and the rapid-prototyping method, and then also uses archwires which are manufactured by a computer-controlled bending machine. This system however is limited given greatly crowded teeth and large rotations, despite this unique, extremely large and cost-intensive effort.

It is evident that a large number of the most varied, highly complicated parts are offered for the 28 teeth of the human which however do not aid the dentist in carrying out his work in suitably precise manner.

In addition, the above described are limited because the patient may prevent the technical precision with which the brackets are manufactured from being conferred to the teeth, due to his limited opening of the mouth, his limited willingness to keep still, on account of the saliva flow and the tone of the lips, cheeks and tongue.

PCT Publication No. WO 03/075782 discloses the bonding of orthodontic fixing elements in a precise position on the dental surface is extremely difficult. The invention relates to a kit for this purpose, consisting of orthodontic fixing elements, whose bonding surface is curved in a convex manner in at least one direction. This ensures that the shape of the element is adapted to the tooth by means of the adhesive. According to the invention, a protector, equipped with a recess that forms the complement of the orthodontic fixing element, is provided. The orthodontic fixing element comprising the protector is applied by being held in an applicator, equipped with various directional locators, by means of a positive-fit, in such a way that a correct positioning can be clearly identified.

SUMMARY OF THE INVENTION

An orthodontic bracket is provided. The inventive orthodontic bracket is suitable for use with metal ligatures, while permitting the use of other fixation systems such as rubber bands or springs.

The inventive orthodontic bracket allows the physical and geometric configuration of an orthodontic archwire to be transmitted onto the tooth in a freely selectable and very controlled manner, and specifically, the freely selectable force with which the orthodontic archwire is fastened on the bracket. The transmission of the physical and geometric configuration of the orthodontic archwire onto the bracket is affected independently of the geometry of the bracket or of the bracket slot, in contrast to brackets known in the art, but the inventive bracket is solely dependant on the freely selectable application of force by the fixation aid.

In one embodiment, the inventive bracket may be converted infinitely into a 0.018 inch (0.46 mm) times 0.022 inch (0.56 mm) slot bracket, or, in another embodiment, it may be converted into a bracket having the dimensions of 0.022 inch (0.56 mm) times 0.025 inch (0.65 mm).

The inventive orthodontic bracket allows a dentist, during the treatment, to utilize adjustment wedges, thus permitting him to achieve a high precession of the system. It also allows the dentist to use orthodontic archwires which are significantly larger in cross section than that of brackets known in the art.

BRIEF DESCRIPTION OF THE DRAWINGS

The present invention will be described in greater detail in the following detailed description, with reference to the accompanying drawings, wherein.

DETAILED DESCRIPTION OF THE INVENTION

Figure 1:
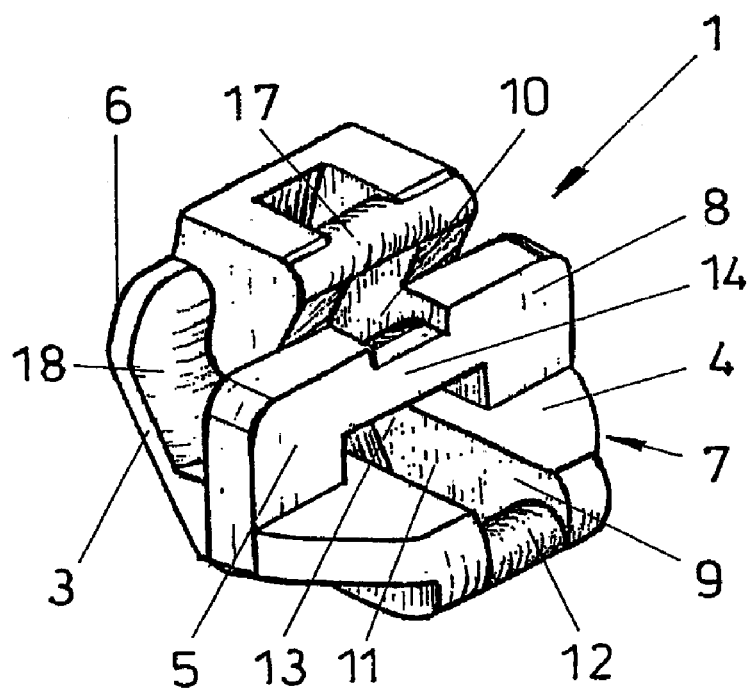
FIG. 1 shows a perspective view of an embodiment of an orthodontic bracket.
Figure 4:
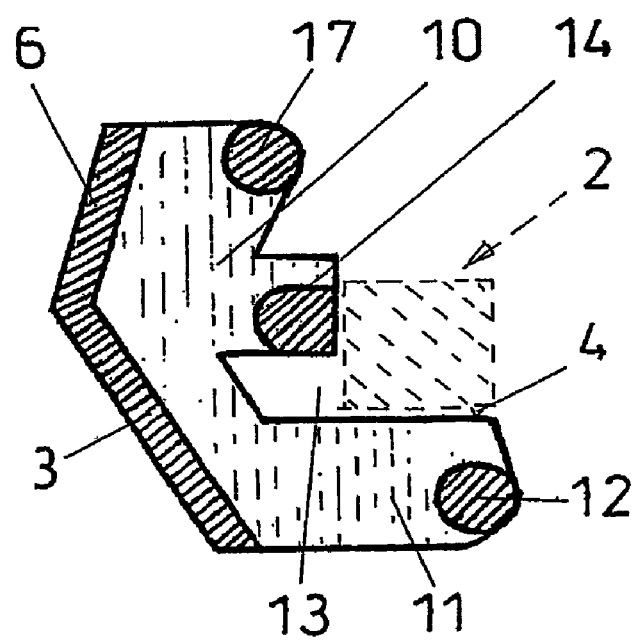
FIG. 4 shows a vertical cross-sectional view of the bracket shown in FIG. 1.
Figure 5:
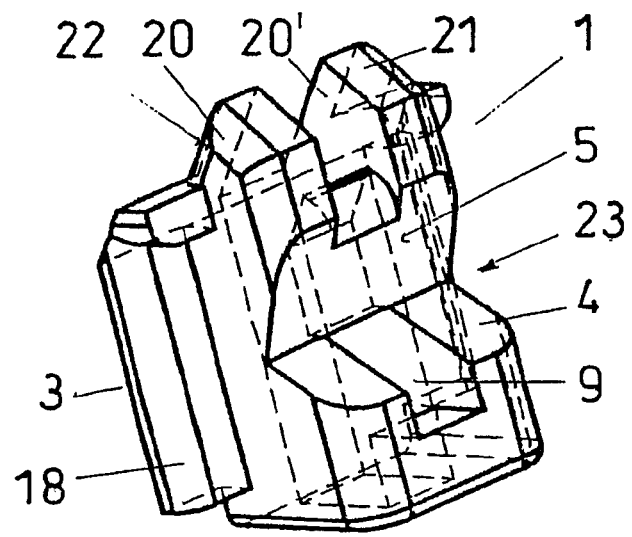
FIG. 5 shows a perspective view of another embodiment of the inventive orthodontic bracket.
Figure 6:
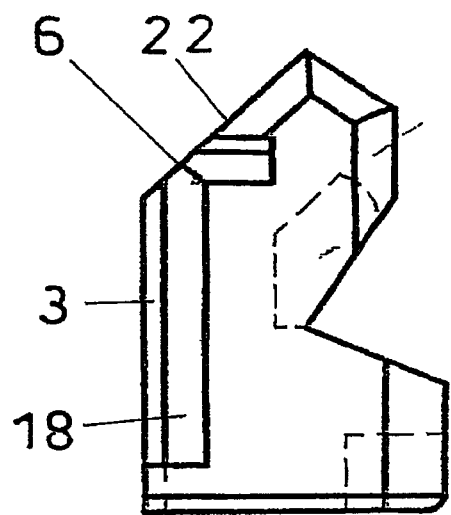
FIG. 6 shows a side view of the bracket shown in FIG. 5.
Figure 7:
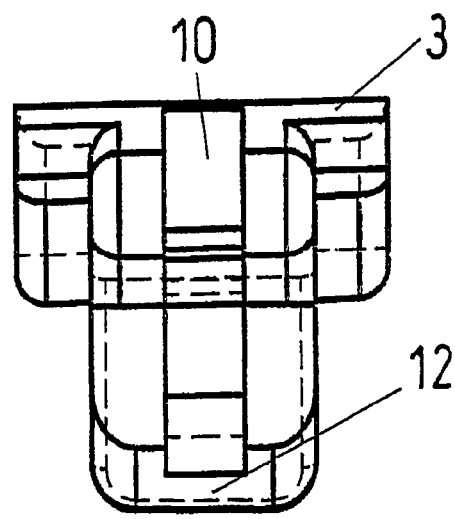
FIG. 7 shows a side view of the bracket shown in FIG. 5.
Figure 8:
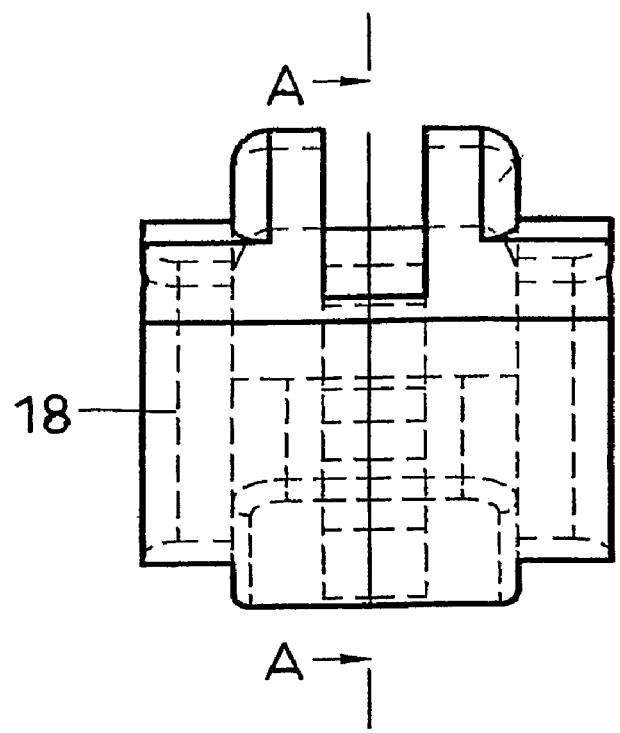
FIG. 8 shows a rearward view of the bracket shown in FIG. 5.
Figure 9:
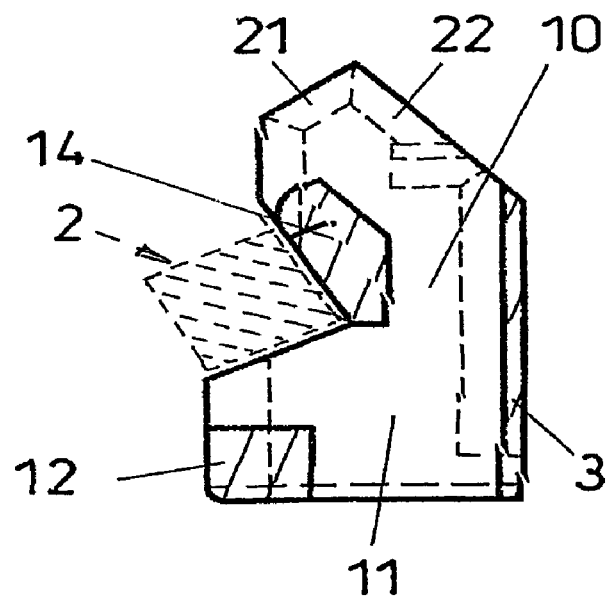
FIG. 9 shows a vertical cross-sectional view of the bracket shown in FIG. 8.
Figure 10:
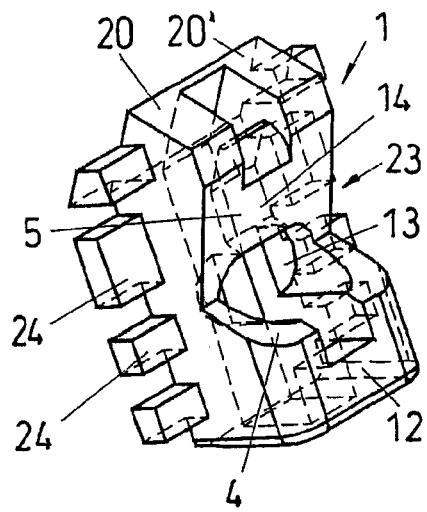
FIG. 10 shows a perspective view of yet another embodiment of the inventive bracket.
Figure 11:
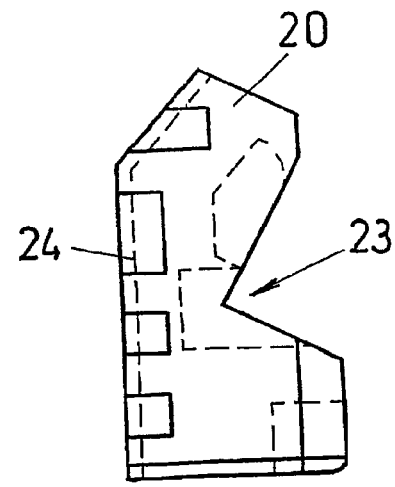
FIG. 11 shows a side view of the bracket shown in FIG. 10.
Figure 12:
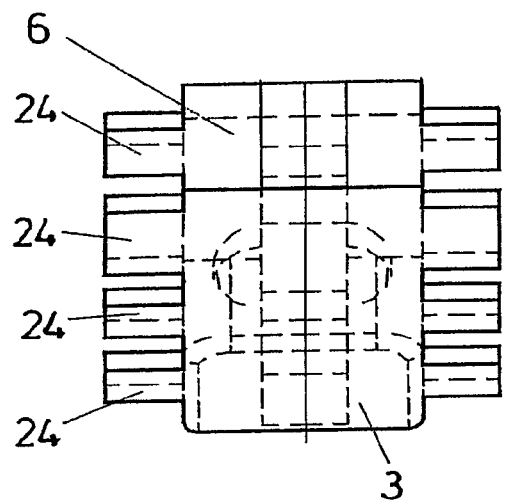
FIG. 12 shows a rearward view of the bracket according to FIG. 10.
Figure 13:
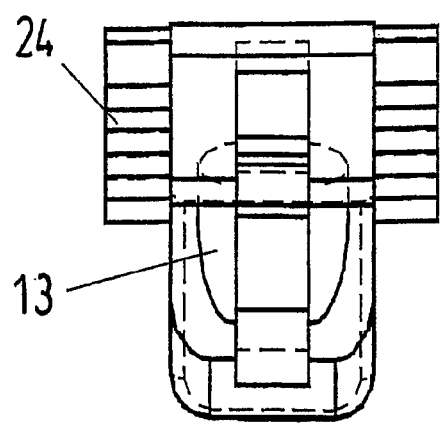
FIG. 13 shows a top view of the bracket according to FIG. 10.

FIG. 1 shows an embodiment of the inventive orthodontic bracket 1. As shown in FIG. 4, an archwire 2 bears on the orthodontic bracket 1. The archwire 2 corresponds to the state of the art and forms a precondition for application of the bracket 1, but is not part of the invention. Archwires of this type are mainly manufactured of steel and titanium alloys and exert a force on the bracket dependent on their elastic property. The orthodontic bracket 1 may be connected to the archwire 2 with a non-positive and/or positive fit in different manners, which are not shown in the figures.

The inventive orthodontic bracket may be manufactured of various materials, including, but not limited to, various metal alloys, ceramic, sapphire glass and plastic.

Figure 2:
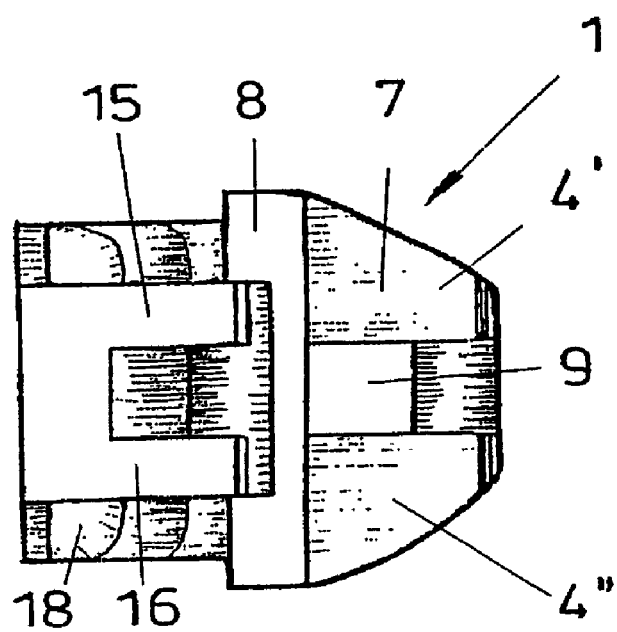
FIG. 2 shows a top view of the bracket of FIG. 1.
Figure 3:
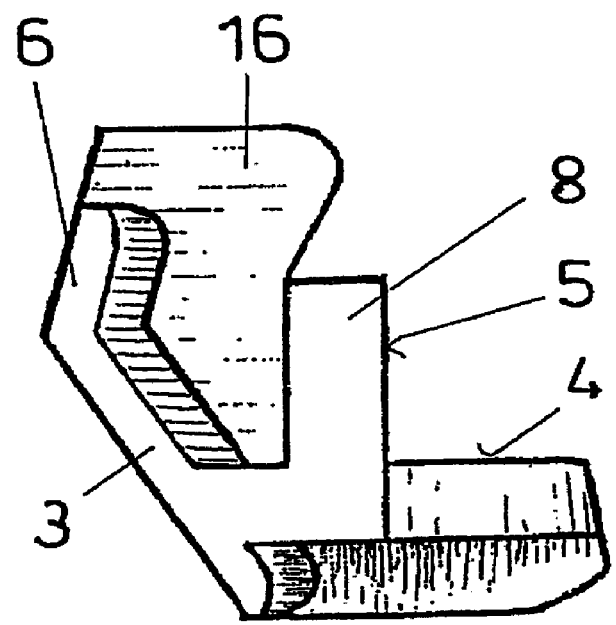
FIG. 3 shows a side view of the bracket of FIG. 1.

Orthodontic bracket 1 comprises a rear wall 3 as well as two guide surfaces 4 and 5 running at right angles to one another. The shaping of the rear wall 3 may in principle be infinite. The rear wall 3 is bent away from the tooth surface in the buccal or lingual direction, at the end situated in the occlusion direction. This bent away end of the rear wall 3 situated in the occlusal direction is indicated at element 6. A support 7 is integrally formed on the rear wall 3. The relative inclination position of the support in relation to the rear wall 3 is thus irrelevant. The support 7 has a first guide surface 4. A wall 8 running perpendicular to the first guide surface 4, hereinafter called perpendicular wall 8, stands on the support 7. The perpendicular wall 8 forms a second guide surface 5. The guide surface 5 is exactly orthogonal to the first guide surface 4. The perpendicular wall 8 is arranged distanced to the rear wall 3. It may be manufactured as a separate part, wherein support 7 would have to be corresponding recessed, in order to be able to be pressed therein with a positive fit. It may however also be manufactured as one piece with the remaining bracket 1. In any case, the two guide surfaces 4 and 5 are arranged distanced to the rear wall 3. The support 7 has a central recess 9. This central recess 9 subdivides the first guide surface 4 into two part surfaces 4' and 4", as shown in FIG. 2. These two part surfaces 4' and 4" run in a flush manner in a plane and form guide surface 4. Two passages 10, 11 remain due to this clearance of the two guide surfaces 4 and 5 distanced to the rear wall 3. The passage 10 runs between the rear wall 3 and the perpendicular wall 8. The second passage 11 is then formed by the central recess 9 and runs between the rear wall 3 and below the first guide surface 4. In this manner, the archwire 2 may, for example, be fastened by way of a ligature on the two guide surfaces 4 and 5 by way of leading the ligature through and behind the perpendicular wall 8 and below the first guide surface, so that the ligature encompasses the archwire 2 and presses it with a non-positive fit at least onto the second guide surface 5.

The support 7 is separated by the central recess 9. This separation may be created by a first web 12 connecting the two support parts. The first web 12 allows the archwire 2 to be pressed in the direction of the first guide surface 4 when the ligature on the one hand is guided through behind the perpendicular wall 8 and on the other hand below the first web 12. The first web 12 as a result comes to lie in the gingival direction below the first guide surface 4.

The wall 8 standing perpendicular to the support 7, in the example shown here, has an opening 13 which extends above the first guide surface 4 and as a result, running in the second guide surface 5, defines a second web 14. The opening 13 may be formed wider than the centric recess 9.

Two part walls 15, 16 are integrally formed on the rear wall 3, which run perpendicular to the second guide surface 5 and extend up to and beyond the perpendicular wall 8. The part walls 15, 16 thus with the rear wall 3 or with the bent end 6 of the rear wall form a type of U-shaped channel. This U-shaped channel is designed such that the inner surfaces of the part walls 15, 16 are flush with the inner surfaces of the central recess 9. A third web 17 connecting these two part walls is present between the two part walls 15, 16. This web 17 is indicated as an occlusal web. The occlusal web 17 also serves as a holding attachment for fixation means with which the archwire 2 may be fixed onto the two guide surfaces 4 and 5.

This may be utilized with suitable ligatures, springs of metal, plastic or other known means.

The rear wall 3 as well as its bent end 6 project to the side with respect to the two part walls 15, 16. Lateral lobes 18 remain on account of this, which serve for the embedding in an adhesive mass and accordingly serve for the connection between the bracket and the tooth on which the bracket is attached. These lateral lobes 18 may be subdivided or broken through by perforations, in order to increase the surface area and achieve an intimate connection to the adhesive mass.

A second embodiment of the inventive orthodontic bracket is shown in the FIGS. 5 to 9. The bracket 1 comprises a rear wall 3, a first guide surface 4 and a second guide surface 5. The guide surfaces 4 and 5 here however are not formed by a support and a wall standing perpendicularly thereto, but by two parallel support walls 20 and 20' running in the gingival-occlusal direction. These support walls 20 and 20' project beyond the rear wall 3 in the gingival and in the occlusal direction. The regions of the support walls 20 and 20' which project in the occlusal direction form gable-like ends 21 which form two part surfaces 22 which form a bent end region of the rear wall 3. A corner is cut into the two support walls 20 and 20' in each case, which both together form a right-angled cut-out 23. The right-angled cut-out 23 thus forms the two guide surfaces 4 and 5. The remaining distance between the two support walls 20 and 20' again forms a central recess 9. In principle, the two guide surfaces 4 and 5 are in each case subdivided into two part surfaces by this central recess. Again, at least one first gingivally arranged web 12 crossing the recess 9 is present between the two support walls 20 and 20'. This web runs below the first guide surface 4. A second web 14 which likewise crosses the central recess 9, is arranged such that it runs at least with a part surface in the second guide surface 5. The two guide surfaces 4 and 5 in are turn arranged distanced to the rear wall 3, so that again two passages 10 and 11 remain between the rear wall 3 and the two guide surfaces 4 and 5. These passages 10 and 11 thus run between the rear wall 3 and the first web 12, and run on the other side between the second web 14 and the rear wall 3.

The embodiment of the orthodontic bracket 1 described above is very compact, permitting a particularly small design with a high strength. The sharp-edged configuration is typical of this embodiment. In particular, it should also be noted that the two webs 12 and 14 are designed in a sharp-edged manner, so that they permit a positionally stable fixation of a spring. The sharp edges of the webs lead to a certain notch effect, so that the springs in the edge regions are deformed such that they at least partly come to bear with an exact positive fit. The sharp-edged design extends also onto the anchoring means in the form of lateral lobes 18. The lateral lobes 18 are formed by the rear wall 3 which is designed projecting outwards with respect to the side walls 20, 20'. The sharp-edgedness here is to improve the anchoring in the adhesive mass.

A third embodiment of the inventive orthodontic bracket 1 is illustrated in FIGS. 10 to 13. In this embodiment, the rear wall 3 is closed on the whole surface, up to the uppermost location in the occlusal direction, and the bent end of the rear wall 6 is no longer divided into part surfaces as this is the case in the embodiment shown in FIGS. 5 to 9. The support walls 20 and 20' are again present, just as the angular cut-out 23. The two webs 12 and 14 are also present in this embodiment. Again an opening 13 is formed just as in the first embodiment. Here however, this arched opening 13 not only runs in the guide surface 5 but extends likewise in the first guide surface 4. The purpose of this opening 13 is specifically for forming an opening which serves for the insertion of suitable adjustment wedges. Anchoring means corresponding to the lateral lobes 18 are also present, but these lobes are subdivided so that laterally projecting anchoring pegs 24 are formed by way of this. These anchoring pegs 24 are however functionally equal to the lateral lobes 18. The anchoring pegs 24 however form a larger contact surface, so that the surface on which the adhesion forces of the adhesive mass may act are increased.

Figure 14:
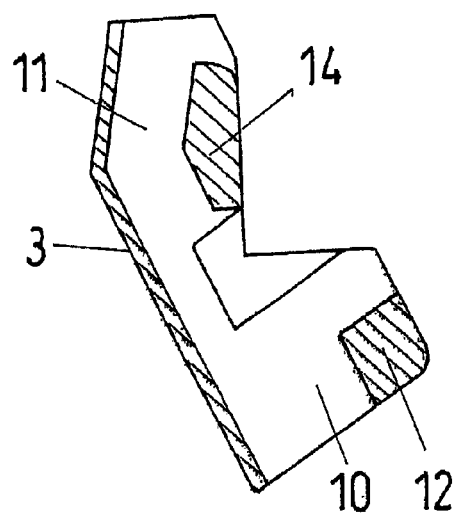
FIG. 14 shows the bracket according to FIG. 9 in a vertical central cross-sectional view.
Figure 15:
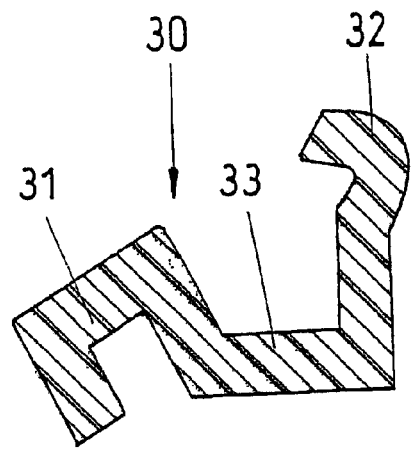
FIG. 15 shows a spring of plastic adapted to the inventive bracket.
Figure 16:
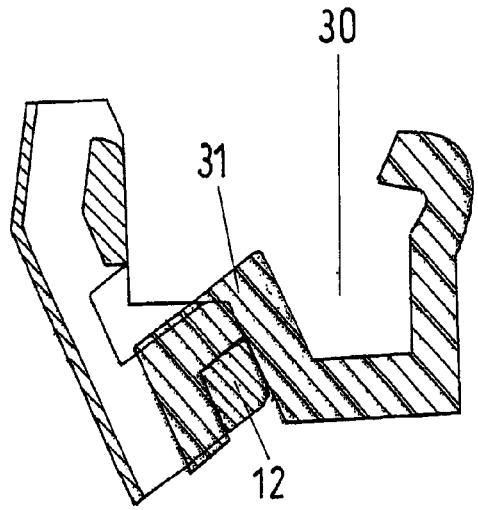
FIG. 16 shows the spring according to FIG. 15 connected to the bracket as shown FIG. 14 in an open position.

The fastening of the archwire 2 on the inventive orthodontic bracket may be achieved by way of ligatures. The wires may be led through the already mentioned passages 10 and 11 or only through one of the two passages. The representation of the ligatures has already been deliberately omitted, since their configuration is accomplished by the applying dentist. In principle however, a loop of wire is always formed and its ends are either clamped on parts of the bracket or the ends are twisted to one another. These possibilities are solved in an ideal manner with the inventive bracket, which is also very suitable for combining with rubber-elastic threads or with spring-elastic wire springs. FIG. 14 once again shows a bracket corresponding to the second embodiment or the third embodiment described above with a gingival web 12, which has a roughly square shape in cross section, and with an occlusal web 14. A spring 30 as shown in FIG. 15, may be used on such a bracket according to FIG. 14. This spring has a roughly S-shaped design in cross section. The spring 30 comprises three parts. A first part forms a retaining hook 31 which is configured such that it is capable of encompassing the first gingival web 12 with a positive and/or non-positive fit. A locking hook 32 is integrally formed at the opposite end of the spring 30, and this is suitable for engaging behind the second or occlusal web 14, in a locking manner. A retaining corner 33 which with regard to shape is adapted to the archwires 2 to be held, remains between the retaining hook 31 and the locking hook 32. As shown in FIG. 16, the spring 30 may firstly be fixed on a web 12 and thereby leaves sufficient space for the dentist to be able to direct and place the archwire 2 before he pivots the spring 30 by 90° about the web 12 until the locking hook 32 is fixed on the second web 14 in a locking manner. The archwire 2 is now positioned exactly on the bracket between the two guide surfaces 4 and 5 on the one hand, and the retaining corner 33 on the other hand. In contrast to conventional brackets with U-shaped slots, adaptations to the applied archwires are possible by way of differently shaped springs. The more flexible fixation of an archwire on the inventive orthodontic bracket permits a better control and a simpler correction of the tooth positioning.

Figure 18:
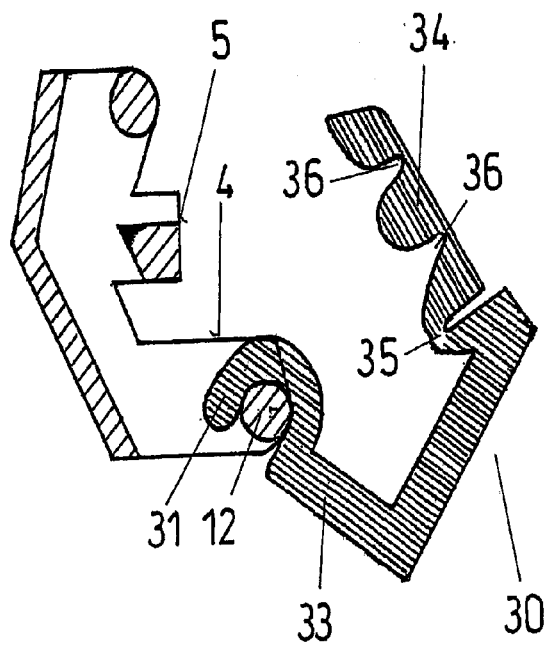
FIG. 18 shows the a bracket of FIG. 4, with another spring element shown in the open position.
Figure 19:
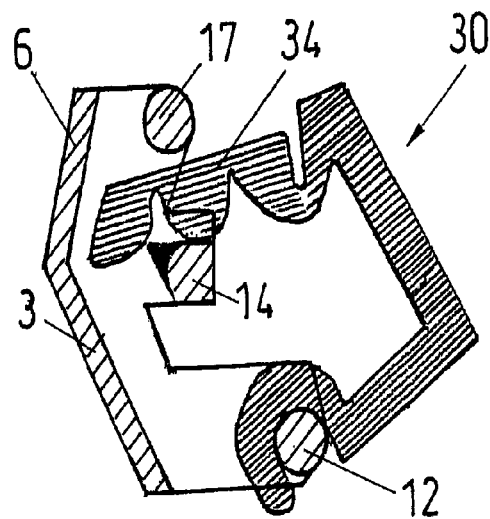
FIG. 19 shows the spring element of FIG. 18 in an intermediate position with the closure procedure.
Figure 20:
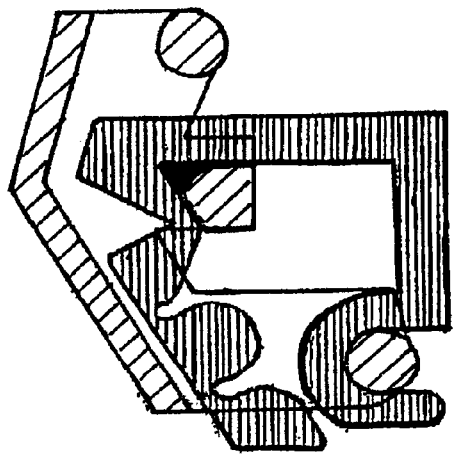
FIG. 20 shows the spring element of FIG. 18 in a closed position.

Another embodiment of a spring 30 is shown in FIGS. 18 to 20. The embodiment shown here is in particular suitable for use on a bracket of the first embodiment described above. The spring 30 shown here practically forms a complete loop in the assembled condition. This spring 30 comprises a retaining hook 31 as well as a retaining corner 33. Here a fixation tab 34 is integrally formed on the retaining corner 33 instead of a locking hook 32. This fixation tab 34 is connected to the retaining corner 33 via a film hinge 35. A fixation tab 34 is elastically deformable by way of two bending grooves 36 in order to simplify the attachment of the spring on the bracket. In FIG. 18, it is shown how the spring 30 is fixed on the gingival web 12, whilst simultaneously the two guide surfaces 4 and 5 are freely accessible and permit the application of the archwire. When the archwire is attached, one pivots the spring 30 by about 90° and then leads the fixation tab 34 between and through the two webs 14 and 17, wherein the fixation tab 34 abuts the rear wall 3 or the angled end 6, whereupon, amid further rotation and application of pressure, the fixation tab 34 curves around the two bending grooves 36 and is displaceable behind and through the web 12 along the rear wall 3, so that the end of the fixation tab 34 comes to lie practically behind the retaining hook 31 and as a result renders its disengagement impossible. The retaining hook 31 may only be disengaged when the fixation tab 34 is again pulled back in the same manner as it was inserted.

Figure 17:
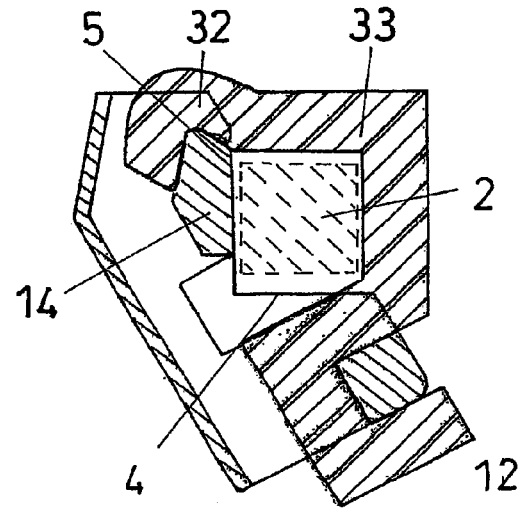
FIG. 17 shows the spring according to FIG. 15 connected to the bracket as shown FIG. 14 in a closed position.
Figure 21:
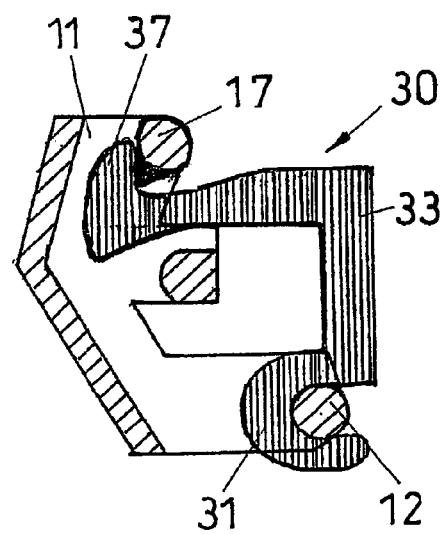
FIG. 21 shows an alternative embodiment of a spring element in the closed position.

Another embodiment of spring 30 is shown in FIG. 21. This spring 30 also has a retaining hook 31 which may be fixed on the gingival web 12 and is integrally formed on the one retaining corner 33. A differently shaped locking hook is however integrally formed at the other end of the retaining corner 33 and is formed as a locking bead 37. In contrast to the embodiment shown in FIGS. 15 to 17, this locking bead 37 does not engage over the occlusal web 17, but below it. In order to release this spring 30, the dentist may press on the locking bead 37 through the upper passage 11, and simultaneously exert a rotational movement.

Figure 22:
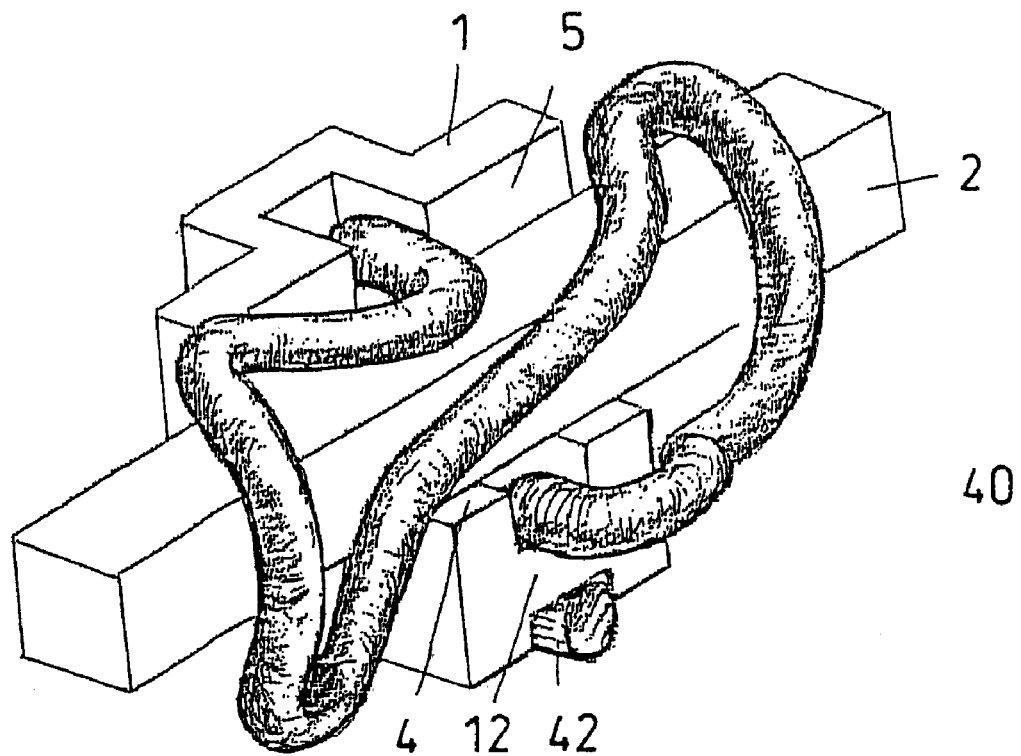
FIG. 22 shows the bracket combined with an 8-shaped spring of wire.
Figure 23:
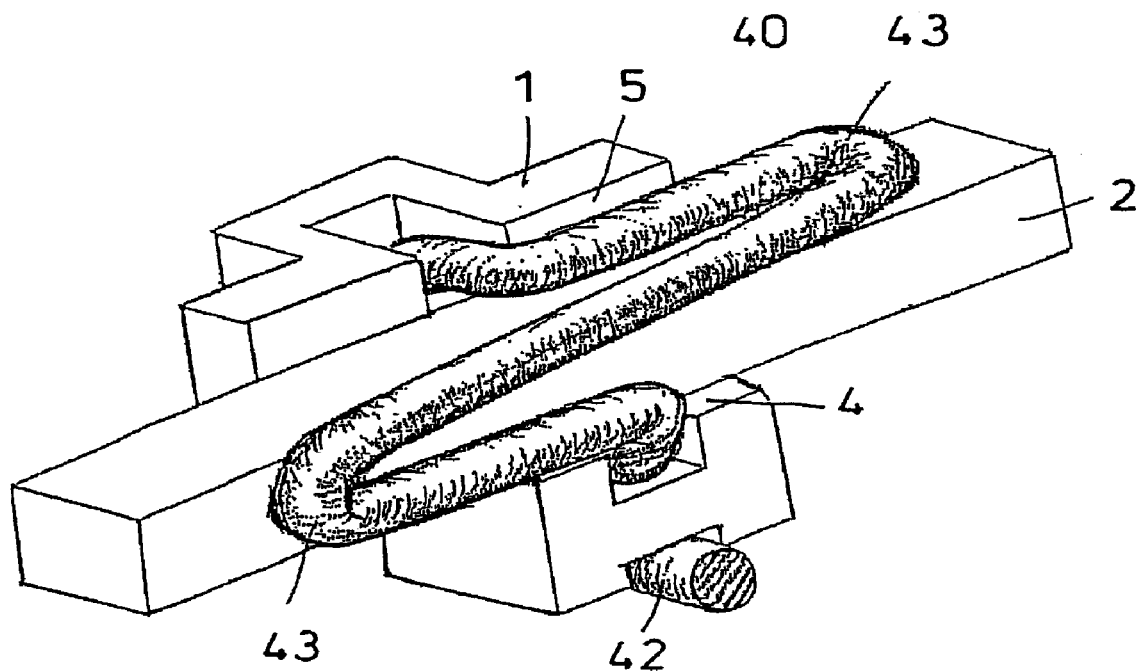
FIG. 23 shows an S-shaped spring of wire combined with the bracket.

Alternative embodiments of a spring 40 are shown in the FIGS. 22 and 23. The orthodontic bracket here is merely shown in a symbolic manner with the two guide surfaces 4 and 5 on which the archwire 2 lies in a bearing manner. A spring of wire is applied over the archwire 2. The spring-elastic wire in the embodiment according to FIG. 22 is roughly bent into the shape of an eight, wherein the middle crossing point is not achieved, but here the two wire ends are shaped such that they may be fixed behind corresponding webs. The spring 40 which roughly forms an eight is in turn bent in a spatially curved manner, in order to lie with its curvature over the archwire 2. In FIG. 22, the spring 40 is shown in the perspective representation of an eight shape of the spring wire. The ends of the spring wire are shaped into fixation hooks 42, of which only the lower fixation hook which engages behind the gingival web 12 is partly evident, whilst the upper fixation hook may not be seen.

The embodiment illustrated in FIG. 23 shows a roughly S-shaped spring of wire. In principle therefore two elongate loops 43 are formed, of which the one loop presses onto one side surface of the archwire 2, whilst the other elongate loop presses onto a side surface of the archwire 2 which runs perpendicular thereto, and thus presses the archwire 2 onto the two guide surfaces 4 and 5. These springs 40 too comprise corresponding fixation hooks 42 which may be held engaging around two corresponding webs.

Figure 24:
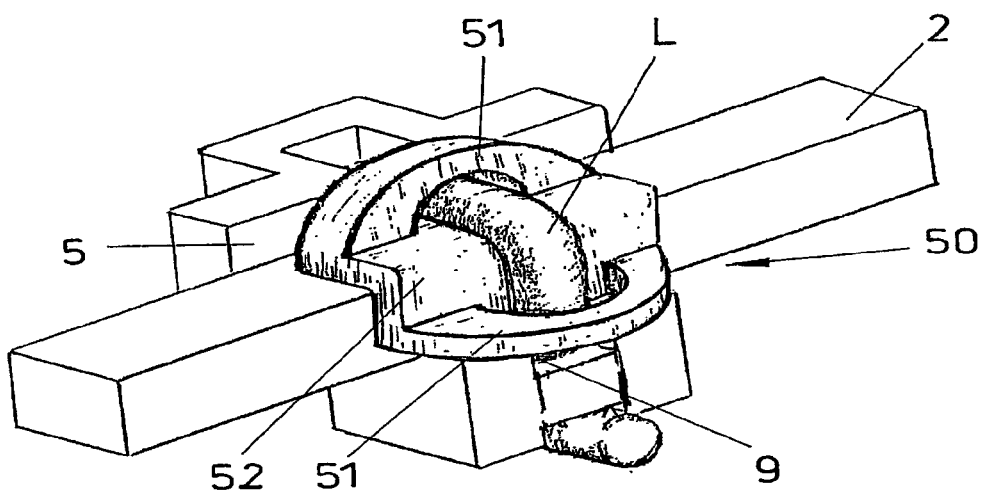
FIG. 24 illustrates the use of a spring which is actively bent and held on the bracket with a ligature.
Figure 25:
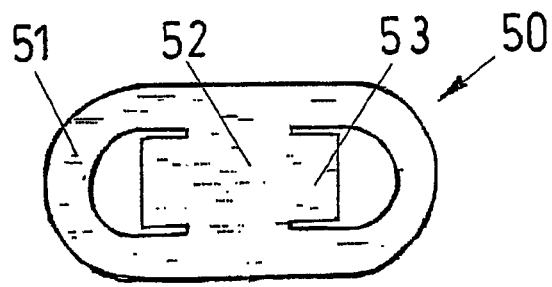
FIG. 25 shows the punch-shape of the spring of FIG. 24.
Figure 26:
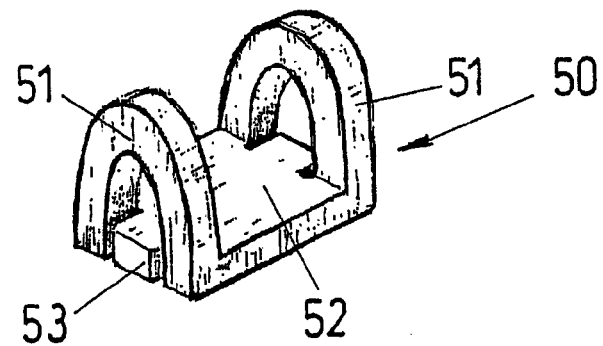
FIG. 26 shows the spring of FIG. 24 after shaping into a passive shape.

Another embodiment of spring 50 is shown in FIGS. 24 to 26 which itself does not create a non-positive fit connection but only together with a metal ligature. The active application is shown in FIG. 24. Again the orthodontic bracket is 1 is merely shown schematically. Again an archwire 2 bears on the two guide surfaces 4 and 5, wherein the guide surface 4 is covered here and is therefore not evident. The spring 50 is shown in the bent, active condition and serves as an active intermediate layer between a ligature L and the archwire 2. In principle, the spring presses the archwire 2 onto the bracket and thus changes the position of the tooth in the desired manner. In particular, as already previously described, if the archwire 2 does not bear on the two guide surfaces 4 and 5 in a large-surfaced manner, the spring 50 acts practically as a rubber underlay disk.

As shown in FIG. 26, the spring 50 may be flat in a middle region 52 and be provided at its two ends with passage loops 51. The middle region 52 may however also be designed as an angularly bent part, as for example shown in FIG. 24. Finally also, as shown in FIG. 25, the complete elastic spring element 50 may be manufactured in a flat manner. In this case, the two passage loops 51 and the middle region 52 lie in one plane. In all cases however, the middle region 52 comprises tongue-like continuations 53, which for the simplified alignment with the application above or below the archwire 2, engage into the central recess 9 in an aligning manner.

Figure 27:
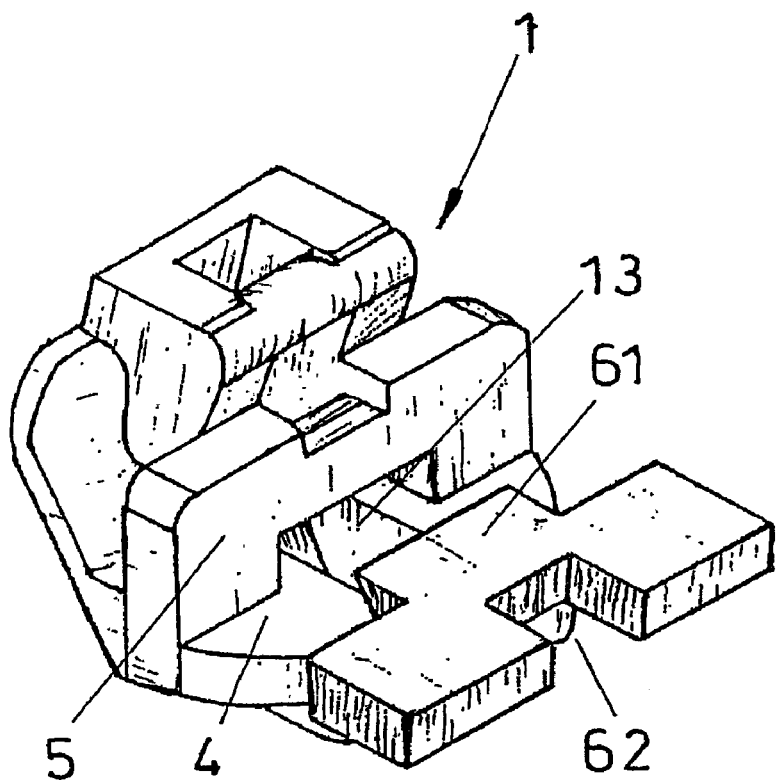
FIG. 27 shows the bracket of FIG. 1 combined with an insertable wedge.
Figure 28:
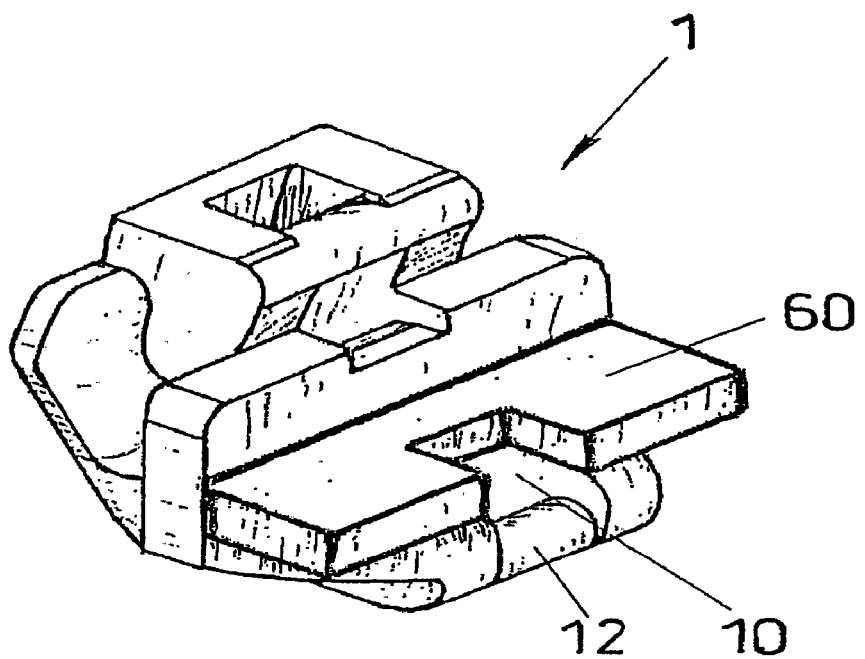
FIG. 28 shows the wedge of FIG. 27 introduced in the end position.
Figure 29:
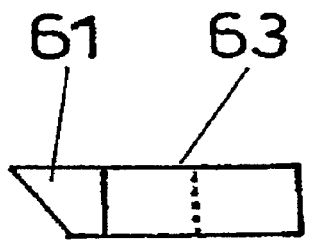
FIGS. 29 to 31 show side views of three different embodiments of wedges.
Figure 30:
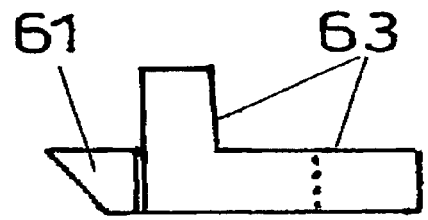
Figure 31:
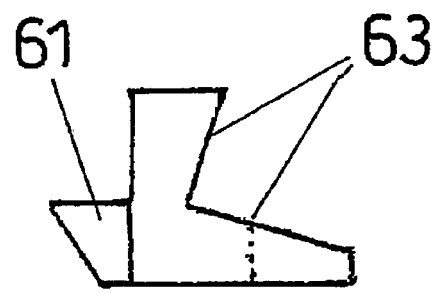
Figure 32:
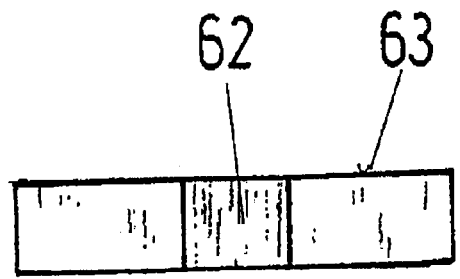
FIG. 32 shows a front view of the wedge according to FIG. 29.

FIGS. 27 and 28 illustrate alternative embodiments of the inventive orthodontic bracket, which may be used with adjustment wedges 60. The opening 13 acts as a key/lock for an adjustment wedge 60 which accordingly comprises a centring tongue 61. At the end side lying opposite the centring tongue 61, the adjustment wedge 60 comprises an indentation 62 which serves for keeping free the passage 10 behind the gingival web 12. In FIG. 27, the adjustment wedge is basically shown in a position during assembly, whilst FIG. 28 shows the adjustment wedge 60 in the assembled, final condition on the bracket 1. FIGS. 29 to 33 show different embodiments forms of the adjustment wedge. Whilst FIG. 29 shows a side view of the adjustment wedge as shown in the FIGS. 27 and 28, the embodiments according to the FIGS. 30 and 31 are showed from the same view but with a different shape.

Figure 33:
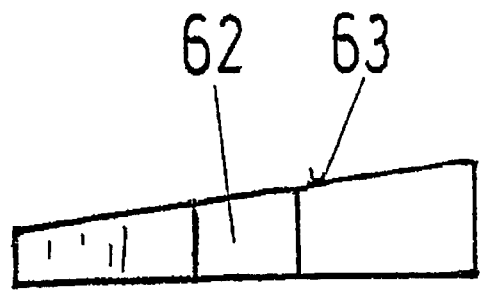
FIG. 33 shows a front view of a wedge with an inclined guide surface.

By way of the wedge according to FIG. 29, one may achieve a vertical tooth displacement or a displacement parallel to the first guide surface 5. The embodiment according to FIG. 30 permits the parallel displacement with respect to the guide surface 4 as well as the guide surface 5. With the embodiment according to FIG. 31, the tooth axis, or the two guide surfaces 4, 5 are pivoted by a certain angle with respect to the longitudinal axis of the archwire. The view according to FIG. 32 again shows the wedge 60 as represented in the FIGS. 27 and 28 as well as FIG. 29, but in the view from the front with a view onto the indentation 62. FIG. 33 shows an alternative of such a wedge in the same view, wherein here the wedge has a rest surface which permits an inclination of the tooth axis in the running direction of the archwire (change of the angulation). Adjustment surfaces 63 are provided to these different embodiments of the adjustment wedges 60, which run parallel or inclined to the guide surfaces and by way of these, one may carry out orthodontically necessary correctional inclinations or fine adjustments. In/out values and/or angulation values and/or inclination—or torque values may be set in by way of these adjustment wedges 60 with the adjustment surfaces 63.

A great advantage of the orthodontic bracket according to the invention described here lies in its simplicity in the variety of its application and the large possibilities of adaptation. From this it results that much lower number of different brackets is required compared to known systems. It is even possible to carry out the required corrections on all teeth with only a single embodiment.

While certain embodiments of the present invention have been described, it will be understood that various changes may be made in the above invention without departing from the scope of the invention. It is intended that all matter contained in the above description or shown in the accompanying drawings shall be interpreted as illustrative and not in a limiting sense.

The invention claimed is:

1. An orthodontic bracket, comprising:
    (a) a rear wall configured for coming to rest on a buccal or lingual tooth surface;
    (b) a support integrally formed on the rear wall;
    (c) a first guide surface provided on the support, the first guide surface being subdivided into two part surfaces by a central recess provided in the support;
    (c) a first gingival web that runs below the first guide surface and extends between the two part surfaces;
    (d) a perpendicular wall that stands on the first guide surface and forms a second guide surface, the perpendicular wall comprising an opening positioned above the central recess and extending above the first guide surface, thereby forming a second occlusal web that runs above the first guide surface; and e) two support walls integrally formed on the rear wall, wherein the support walls run perpendicular to the second guide surface, and extend up to and beyond the perpendicular wall, wherein inner surfaces of the support walls are flush with inner surfaces of the central recess, and the two support walls are connected by a third occlusal web lying above the perpendicular wall, wherein the first and second guide surfaces run at right angles to one another, are arranged distanced to the rear wall, and are capable of guiding an archwire with a rectangular cross section, and wherein a second passage is left free between the first gingival web and the rear wall, and a first passage is left free between the second occlusal web and the rear wall.

2. The orthodontic bracket of claim 1, wherein the first gingival web is arranged between the two part surfaces and crosses the central recess.

3. The orthodontic bracket of claim 1, wherein the opening is wider than the central recess.

4. The orthodontic bracket of claim 1, wherein the rear wall comprises lobe-like lateral regions which serve for embedding the orthodontic bracket in an adhesive mass for fastening on a tooth surface.

5. The orthodontic bracket of claim 1, wherein the first gingival web and the second occlusal web each have a sharp-edged cross section.

6. The orthodontic bracket of claim 1, wherein the first gingival web has an at least approximately square cross section.

7. An orthodontic device comprising an orthodontic bracket of claim 1 and a rubber-elastic spring that can be attached over the archwire and is capable of being held on the first gingival and second occlusal webs and pressing the archwire onto the first and second guide surfaces, the spring being provided with a retaining hook for engaging at least one of the first gingival and second occlusal webs, wherein the spring is pivotable about the first gingival web and is lockable on the second occlusal web with a locking hook, and wherein, in the pivoted-in condition, a retaining corner of the spring bears on the archwire with a positive and/or non-positive fit.

8. An orthodontic device comprising an orthodontic bracket of claim 1 and a spring of wire which is held by the first gingival web and the second occlusal web in a lockable rear engagement and can be attached over the archwire.

9. The orthodontic device of claim 8, wherein the spring is bent in an S-shaped or 8-shaped manner.

10. The orthodontic bracket of claim 1, further comprising an adjustment wedge lying on at least one guide surface.

11. The orthodontic bracket of claim 10, wherein the adjustment wedge comprises a centering tongue which can be inserted into the opening of the bracket.

12. The orthodontic bracket of claim 10, wherein the adjustment wedge comprises an indentation which, in an assembled condition of the adjustment wedge, leaves free a passage behind at least one of the first gingival web and the second occlusal web.

13. The orthodontic bracket of claim 10, wherein the adjustment wedge comprises at least one adjustment surface parallel or inclined to the first guide surface or the second guide surface, by way of which at least one of the angulation value and the torque value may be corrected in a settable manner.

* * * * *